(12) United States Patent
Douglass et al.

(10) Patent No.: US 8,252,719 B2
(45) Date of Patent: Aug. 28, 2012

(54) AGROCHEMICAL COMPOSITIONS

(75) Inventors: Andrew Douglass, Cranbury, NJ (US); Jeffrey David Fowler, Greensboro, NC (US)

(73) Assignee: Syngenta Limited, Guildford (GB)

( * ) Notice: Subject to any disclaimer, the term of this patent is extended or adjusted under 35 U.S.C. 154(b) by 526 days.

(21) Appl. No.: 10/432,458

(22) PCT Filed: Dec. 3, 2001

(86) PCT No.: PCT/EP01/14121
§ 371 (c)(1),
(2), (4) Date: Nov. 10, 2003

(87) PCT Pub. No.: WO02/45507
PCT Pub. Date: Jun. 13, 2002

(65) Prior Publication Data
US 2005/0043182 A1 Feb. 24, 2005

Related U.S. Application Data

(60) Provisional application No. 60/251,189, filed on Dec. 4, 2000.

(51) Int. Cl.
*A01N 25/00* (2006.01)

(52) U.S. Cl. .................................................. 504/116.1

(58) Field of Classification Search .................. 504/363; 514/229.2, 383, 460, 539, 937
See application file for complete search history.

(56) References Cited

U.S. PATENT DOCUMENTS

| | | | |
|---|---|---|---|
| 5,160,528 A | 11/1992 | Chaudhuri et al. | |
| 5,444,078 A * | 8/1995 | Yu et al. | 514/372 |
| 5,597,792 A * | 1/1997 | Klier et al. | 510/417 |
| 5,597,840 A | 1/1997 | Moore | |
| 5,834,400 A | 11/1998 | Goehner, Jr. et al. | |
| 2003/0170284 A1 * | 9/2003 | Dorschner et al. | 424/405 |

FOREIGN PATENT DOCUMENTS

| | | | |
|---|---|---|---|
| DE | 19740452 | * | 3/1999 |
| WO | 9213454 | | 8/1992 |
| WO | WO-0067573 | * | 11/2000 |

OTHER PUBLICATIONS

Scientific Physic, Fats, Oils, Fatty Acids, Triglycerides.*

* cited by examiner

*Primary Examiner* — Alton Pryor
(74) *Attorney, Agent, or Firm* — Kody Jones

(57) ABSTRACT

Microemulsifiable hydrophobic agrochemical concentrates are provided which are a combination of (A) an alkyl alkanoate with (B) a poyhydric alcohol, a polyhydric alcohol condensate or a mixture thereof and (C) at least one surfactant; the novel compositions are storage stable, easy to apply, ecological and toxicologically favorable and, upon dilution with water, are useful as plant treatment compositions that have good biological efficacy in the target application.

61 Claims, No Drawings

AGROCHEMICAL COMPOSITIONS

This application is a National Stage application of PCT/EP01/14121, filed on Dec. 3, 2001, which claims priority to U.S. provisional application 60/251,189, filed on Dec. 4, 2000.

1. TECHNICAL FIELD

The present invention relates to liquid agrochemical compositions for application of an agriculturally active chemical to a plant, a pest or to a locus thereof. In particular, this invention relates to liquid compositions of agriculturally active chemicals that are in the form of microemulsions or microemulsion preconcentrates, the preparation of such compositions and a method of using such compositions to combat pests or as plant growth regulators.

2. BACKGROUND OF THE INVENTION

When agriculturally active chemicals (agrochemcials) are relatively water soluble, preparing, storing, and shipping the same in a commercially acceptable form can be relatively clear-cut. However, many agrochemicals are hydrophobic and formulators are often confronted with difficulties in finding a suitable means for preparing these materials in stable formulations that deliver maximum loading of active ingredient per unit volume to the end-user. One means of doing this is to prepare dry formulations such as wettable dispersible granules (WDG's) or wettable powders (WP's) encapsulated, for example, in water soluble bags or containers. Although such dry formulations are attractive not only from a loading delivery viewpoint, but also from a handling and/or worker safety viewpoint, not all hydrophobic agrochemicals are able to be dry formulated.

The most straight-forward approach to preparing concentrated liquid formulations with agrochemicals having limited aqueous solubility has been through the use of aromatic organic solvent systems. In such systems, aromatic organic solvents such as xylene or kerosene are used to solubilize the agrochemical compound of interest.

Commonly, surfactants are added to the agrochemical-solvent compositions to form emulsion concentrates. The surfactant-emulsifiers interact with the agrochemicals in a number of ways both before and during actual use, i.e., application to the site. The surfactants can initially disperse and/or emulsify the agrochemical in the solvent or in an inert carrier media and, for example, with herbicides, the surfactant composition may also act as a penetrant, spreader, sticker, stabilizer, and wetting agent. The surfactant composition may affect the rate of drying of a droplet on a plant and the nature of a residue liquid, or crystal. The surfactants may also influence the weathering characteristics of an agrochemical, including its rewetting characteristics and rainfastness.

The presence of the volatile organic compounds in these formulations, together with the surfactants, enable stable emulsifiable agrochemical concentrates (EC's) to be prepared. Although such EC formulations have played and continue to play a major role in the agrochemical market, they have a significant drawback in that the formulations are commonly based on the use of considerable quantities of the highly volatile organic compounds. Some of these highly volatile organic compounds are not entirely satisfactory; in particular with respect to their ecological and toxicological properties. One additional characteristic, which is growing in importance in the agricultural chemical marketplace, is the property of reduced eye irritation as measured by published U.S. Environmental Protection Agency regulations.

Microemulsion (ME) technology has been explored as a possible approach to address the above-noted drawbacks of agrochemical EC formulations. In general, microemulsions are characterized by particle sizes between 3 and 10 nm. The small particle size allows for the emulsion to be more stable than an EC formulation. These systems have proven highly useful for such diverse objects as surface cleaners, paint compositions, oil recovery systems, cosmetic preparations, drug delivery and pesticidal formulations. The desired properties of these compositions are obviously quite varied depending on the intended application, but all of these compositions have the advantage of limited use of undesirable solvents and formation of a highly stable emulsified form.

There is still a need for further microemulsifiable agrochemical concentrates that are suitable for a broad range of agriculturally active ingredients, have a high biological activity in the target application, have good chemical and physical stability under a severe range of conditions that can be experienced in the marketplace, have good ecological and toxicological properties, exhibit reduced eye irritation and be readily water-dilutable to form a microemulsion.

3. SUMMARY OF THE INVENTION

It has been found that the combination of (A) an alkyl alkanoate with (B) a polyhydric alcohol, a polyhydric alcohol condensate or a mixture thereof and (C) at least one surfactant is a very advantageous system for microemulsifiable hydrophobic agrochemical concentrates; the novel compositions are storage stable, easy to apply, ecological and toxicologically favorable and, upon dilution with water, are useful as agrochemical compositions that have good biological efficacy in the target application.

Accordingly, the present invention provides a microemulsifiable, storage stable, liquid, agrochemical concentrate comprising a hydrophobic agrochemical or mixture of agrochemicals dissolved in a solvent blend comprising an alkyl alkanoate and a polyhydric alcohol, a polyhydric alcohol condensate or a mixture thereof and comprising at least one hydrophylic surfactant. The relative proportion of said hydrophobic agrochemical or mixture of agrochemicals, solvent blend and hydrophilic surfactant being such that upon dilution of said concentrate with adequate water, a stable oil-in-water microemulsion is spontaneously formed. The microemulsifiable concentrates of the invention exhibit reduced eye irritation and, in the preferred embodiments, meet the requirements for a Caution Signal Word as defined in the regulations of the U.S. Environmental Protection Agency (EPA) as of November 2000. This Signal Word classification is highly valued for a product in the agricultural chemical marketplace. In a preferred embodiment, the microemulsifiable concentrate (MEC) and corresponding microemulsion formed therefrom are substantially clear. In another preferred embodiment, the MEC and corresponding microemulsion are substantially odorless. In a highly preferred embodiment, the MEC and corresponding microemulsion are substantially clear, substantially odorless, and meets or exceeds the requirements for a "Caution Signal Word".

5. DETAILED DESCRIPTION OF THE INVENTION

The present invention provides a microemulsifiable agrochemical concentrate ("MEC") that upon dilution with adequate water forms a stable oil-in-water microemulsion useful for, inter alia, the treatment of plants comprising:

(a) a hydrophobic agrochemical or mixture of hydrophobic agrochemicals, (b) (i) a first solvent which is an alkyl alkanoate;
   (ii) a second solvent which is a polyhydric alcohol, a polyhydric alcohol condensate or a mixture thereof; and (c) at least one surfactant;

the relative proportions of components (a), (b), and (c) being such that upon dilution of said concentrate with adequate water, a stable oil-in-water microemulsion is spontaneously formed.

The term "agrochemical" as used herein means a chemical substance, whether naturally or synthetically obtained, which is applied to a plant, to a pest or to a locus thereof to result in expressing a desired biological activity. The term "biological activity" as used herein means elicitation of a stimulatory, inhibitory, regulatory, therapeutic, toxic or lethal response in a plant or in a pest such as a pathogen, parasite or feeding organism present in or on a plant or the elicitation of such a response in a locus of a plant, a pest or a structure. The term "plant" includes but shall not be limited to all food, fiber, feed and forage crops (pre and post harvest, seed and seed treatment), trees, turf and ornamentals. Examples of agrochemical substances include, but are not limited to, chemical pesticides (such as herbicides, algicides, fungicides, bactericides, viricides, insecticides, acaricides, miticides, nematicides and molluscicides), herbicide safeners, plant growth regulators, fertilizers and nutrients, gametocides, defoliants, desiccants, mixtures thereof and the like.

The term "hydrophobic" as used in the present specification with respect to the term "agrochemical" means not soluble in water to an appreciable amount, more specifically having a water solubility of not more than about 2% w/v, more particularly not more than about 1% w/v at 25° C.

The term "surfactant" as used in the present specification means a chemical substance that acts as a surface active agent which can provide foaming, wetting, dispersing and emulsifying properties and which is cationic, anionic, nonionic or amphoteric.

Suitable alkyl alkanoate ester solvents (b)(i) include the $C_6$-$C_{13}$ alkyl $C_{1-4}$ alkanoates such as the oxo-hexyl, oxo-heptyl, oxo-octyl, oxo-2-ethyl-hexyl, oxo-nonyl, oxo-decyl, oxo-dodecyl and oxo-tridecyl formates, acetates, propanoates, and butanoates; preferably the $C_6$-$C_{13}$ alkyl acetates. These materials are generally commercially available or can be readily made by those of ordinarty skill in the art. A number of the foregoing alkyl acetates are commercially available. Particularly advantageous $C_6$-$C_{13}$ alkyl acetates are available from Exxon Mobil Corporation under the general trade designation "Exxate".

Suitable polyhydric alcohols and polyhydric alcohol condensates (b)(ii) include propylene glycol; dipropylene glycol; poly$C_{2-6}$alkylene glycols and derivatives preferably poly$C_{2-6}$ alkylene glycol and derivatives such as polypropylene glycol [M.W. 2000-4000], polyoxyethylene polyoxypropylene glycols, polyoxypropylene polyoxyethylene glycols, diethyleneglycol, polyethylene glycol [M.W. 200-4000 amu], methoxy polyethylene glycols 350, 550, 750, 2000, 5000; glycerol; ethoxylated glycerol; propoxylated glycerol; sugar alcohols and their alkoxylated derivatives such as xylitol, mannitol, sorbitol, ethoxylated sorbitol, hydroxypropyl sorbitol; glyceroltriacetate; hexylene glycol (2-methyl-2,4-pentanediol); 1,3-butylene glycol; 1,2,6-hexanetriol; ethohexadiol USP (2-ethyl-1,3-hexanediol); $C_{15}$-$C_{18}$vicinal glycol and polyoxypropylene derivatives of trimethylolpropane, short-chain up to 7 carbons, preferably up to 4 carbons aliphatic glycols, and glycerine.

In one embodiment of the invention, the MEC comprises, in addition to the blend of first and second solvents (b)(i) an alkyl alkanoate ester and (b)(ii) a polyhydric alcohol, a polyhydric alcohol condensate or a mixture thereof, a further component which is (b)(iii) a water-miscible solvent.

Suitable water-miscible solvents (b)(iii) include tetrahydrofurfuryl alcohol, gamma-butyrolactone, N-methyl-2-pyrrolidone, tetramethylurea, dimethylsulfoxide, N,N-dimethylacetamid and dimethylformamide; preferred are tetrahydrofurfuryl alcohol, gamma-butyrolactone, N-methyl-2-pyrrolidone, triethylphosphate and propylene carbonate.

The surfactant (c) can be a single surfactant, but in preferred embodiments it is most advantageously a blend of surfactants comprising: a first cationic surfactant (c)(i) and a second nonionic surfactant (c)(ii). Each of said first and said second sufactant components may be made up of one or more than one surfactant of the requisite type if so desired.

Examples of such surfactant materials (c) are the following:

(c) (i) Cationic surfactants selected from the group consisting of one or more poly$C_{2-4}$alkoxylated $C_{14-20}$fatty amines, preferably the poly$C_{2-4}$alkoxylated $C_{12-18}$fatty amines, most preferably a poly$C_{2-4}$alkoxylated tallow amine. The poly$C_{2-4}$ alkoxylated portion of this component is preferably present in either 2-8 (more preferably 2-5) repeating units per molecule or the poly$C_{2-4}$alkoxylated portion of this component is preferably present in about 14 to about 18 (more preferably about 16) repeating units per molecule or more preferably is -$[EO]_{2-20}$-; and mixtures thereof. Particularly useful amine compounds include the Toximuls such as TA-2, -3, -4, -5, -6, -7, -7, -8, -9, -10, -11, -12, -13, -14, -15, -16, -17, -18, -19 and -20 (Stepan); and mixtures thereof. Additional suitable cationic surfactants include the fatty acid alkanol amides such as, for example, the Witcamides (Witco).

(c) (ii) Nonionic surfactants selected from the group consisting of (1) a mono $C_{2-6}$alkyl ether of a poly$C_{2-4}$alkylene oxide block copolymer having at least a first polyalkylene oxide block region and a second polyalkylene oxide block region in which the polyalkylene oxide in said first region is different than the polyalkylene oxide in said second region. Preferably, the $C_{2-6}$alkyl ether portion is a $C_{3-5}$alkyl ether, more preferably a $C_4$alkyl ether, of the alkylene oxide block copolymer. Also preferably, the alkylene oxide block copolymer portion is preferably an ethylene oxide/propylene oxide block copolymer. Preferably the ethylene oxide portion represents from about 10 to about 90 mole % to from about 25 to about 75 mole % of the block copolymer. A particularly preferred material is available under the trade name NS-500LQ, available from Witco; (2) a condensation product of castor oil and a poly$C_{2-4}$alkylene oxide. Preferably the alkylene oxide portion is ethylene oxide. Preferably the degree of alkoxylation is from about 10 moles to about 100 moles of alkylene oxide per mole of castor oil, more preferably about 20 moles to about 70 moles of alkylene oxide per mole of castor oil. A highly preferred alkoxylated castor oil is available under the trade name $CO_{360}$, available from Witco.; (3) a mono- or di-ester of a $C_{12-24}$fatty acid and poly$C_{2-4}$ alkylene oxide, where the fatty acid groups may be the same or different. Preferably, the fatty acid groups are the same when two such groups are present. Also preferably, the fatty acid groups are $C_{12-20}$fatty acid groups, more preferably $C_{12-18}$fatty acid groups, most preferably lauroyl, oleic, caprylic or myristoleic. In addition, the poly$C_{2-4}$alkylene oxide portion is preferably polyethoxy and the number of alkylene oxide groups in the polyC$_{2-4}$alkylene oxide portion is preferably from about 2 to about 40 repeating units. Highly preferred materials of this type include Kessco PEG 400DL (Stepan) and Emerest 2620 (Cognis).

In one embodiment of the invention, the MEC comprises, in addition to the blend of first and second surfactants (c)(i) and (c)(ii), a further component which is (c)(iii) an anionic surfactant.

Suitable anionic surfactants (c)(iii) include a poly(oxy-1, 2-ethanediyl)-alpha-C$_{10-15}$alkyl-omega-hydroxy phosphate or sulphate and/or a C$_{10-13}$alkylbenzenesulfonic acid. Preferably, the a poly(oxy-1,2-ethanediyl)-alpha-C$_{10-15}$alkyl-omega-hydroxy phosphate or sulphate is a poly(oxy-1,2-ethanediyl)-alpha-tridecyl-omega-hydroxy phosphate or sulphate. Also, the (oxy-1,2-ethanediyl) portion of the compound is present in about 3 to about 9, preferably about 6, repeating units per molecule. A suitable compound for the poly(oxy-1,2-ethanediyl)-alpha-C$_{10-15}$alkyl-omega-hydroxy phosphate is available as Stepfac 8181 (Stepan). A suitable compound for the C$_{10-13}$alkylbenzenesulfonic acid is Biosoft S-100 (Stepan). Additional suitable anionic surfactants include the phosphate and sulphate derivatives of ethoxylated alkyl phenols such as -[EO]$_{2-20}$-di and tristyrylphenols, nonylphenols, dinonylphenol and octylphenols.

Where salts of the phosphate or sulphate group are desirable, the salt may be a salt with any base so long as the base is not incompatible with any of the other ingredients including the agrochemical. Particularly suitable are the phosphate salts of alkali metals, alkaline earth metals, ammonia or an organic amine, such as morpholine, piperidine, pyrrolidine, a mono-, di- or tri-lower alkylamine, for example ethyl-, diethyl-, triethyl- or dimethyl-propylamine, or a mono-, di- or tri-hydroxy-lower alkylamine, for example mono-, di- or triethanolamine.

In a highly preferred embodiment, component (c) contains each of (c)(i) a polyC$_{2-4}$alkoxylated fatty amine and (c)(iii) a C$_{9-17}$alkyl-(OCH$_2$CH$_2$)$_n$—O-phosphate. Advantageously, the pH of the MEC can be optimized to accommodate a particular agrochemical by adjusting the ratios and amounts of (c)(i) cationic and (c)(iii) anionic surfactants. Still further cationic surfactants can be added to the mixture if desired.

In another highly preferred embodiment, component (c)(ii) contains each of a condensation product of castor oil and a polyC$_{2-4}$alkylene oxide; a mono C$_{2-6}$alkyl ether of a polyC$_{2-4}$ alkylene oxide block copolymer having at least a first polyalkylene oxide block region and a second polyalkylene oxide block region in which the polyalkylene oxide in said first region is different than the polyalkylene oxide in said second region; and a mono- or di-ester of a C$_{12-24}$fatty acid and polyC$_{2-4}$alkylene oxide, where the fatty acid groups may be the same or different. Still further nonionic surfactant can be added if desired.

In a most highly preferred embodiment, component (c) contains each of (c)(i) a polyC$_{2-4}$alkoxylated fatty amine, (c)(ii) a condensation product of castor oil and a polyC$_{2-4}$ alkylene oxide; a mono C$_{2-6}$alkyl ether of a polyC$_{2-4}$alkylene oxide block copolymer having at least a first polyalkylene oxide block region and a second polyalkylene oxide block region in which the polyalkylene oxide in said first region is different than the polyalkylene oxide in said second region; and a mono- or di-ester of a C$_{12-24}$fatty acid and polyC$_{2-4}$ alkylene oxide, where the fatty acid groups may be the same or different and (c)(iii) a C$_{9-17}$alkyl-(OCH$_2$CH$_2$)$_n$—O-phosphate.

In all cases where polyalkylene groups are mentioned, unless otherwise stated, the number of repeating units of alkylene oxide in a molecule may range up to about 110, preferably up to about 50, more preferably from about 2 to about 40. In alkylene oxide chains, the preferred alkylene oxide group is —O—C(R)(R)—C(R)(R)— where each R is independently hydrogen or an alkyl of sufficient carbon atoms to so that in the aggregate all of the carbon atoms between all of the R groups and the 2 backbone carbons satisfy the carbon requirement of the particular alkylene group mentioned for each repeating unit of that type. Hence a propylene oxide group would preferably have one R group as a methyl, while a butylene oxide group would preferably have either on R group as ethyl or two R groups as methyl (which may or may not be on the same carbon atom). Unless stated otherwise, ethylene oxide and propylene oxide groups are the preferred alkylene oxides.

As noted above, the organic solvent blend (b) in which the agrochemical has to be dissolved is a mixture of at least two solvents. A first solvent is (b)(i) an alkyl alkanoate. The second solvent is (b)(ii) a polyhydric alcohol, a polyhydric alcohol condensate or a mixture thereof. Optionally a water miscible solvent (b)(iii) also is used. Occasionally, small amounts of additional water-immisible solvents (b)(iv) may be included where formulation of the other components makes it desirable without departing from the spirit of the invention; however, use of the additional water-immiscible solvents (b)(iv) may not be necessary.

Suitable additional water-immiscible solvents (b)(iv) which may be used in minor amounts in which the agrochemicals may be dissolved are aliphatic and aromatic hydrocarbons such as hexane, cyclohexane, benzene, toluene, xylene, mineral oil or kerosin, mixtures or substituted naphthalenes, mixtures of mono- and polyalkylated aromatics commercially available under the registered trademarks SOLVESSO and SHELLSOL and PETROL SPEZIAL, halogenated hydrocarbons such as methylene chloride, chloroform and o-dichlorobenzene; phthalates, such as dibutyl phthalate or dioctyl phthalate; ethers and esters, such as ethylene glycol monomethyl or monoethyl ether, fatty acid esters; such as cyclohexanone; higher alcohols such as hexanol and octanol; plant oils such as castor oil, soybean oil, cottonseed oil and possible methyl esters thereof; as well as epoxidised coconut oil or soybean oil.

The MEC of the present invention is generally characterized by a density of from about 0.9 to about 1.1 g/ml; a viscosity of from about 20-300 cps at 25° C. measured by using for example a BROOKFIELD viscosimeter with spindles 1 to 3 at 30 rpm; and a pH of from about 3 to about 8. The microemulsion droplet particle size ranges from about 20-300 nm.

Suitable hydrophobic agrochemicals are those which are substantially insoluble in water (solubility is typically not more than about 2% w/v, more particularly not more than about 1% w/v at 25° C.), but soluble in the alkyl alkanoate—polyhydric alcohol blend alone or optionally in combination with a water miscible solvent Agrochemicals include, without being limited to, pesticides. Pesticides, include, without being limited to, herbicides, insecticides, miticides, acaricides, nematocides, ectoparasitcides, fungicides, bacteriocides, algacides, and plant growth regulators. With respect to their chemical constitution, these agrochemicals may belong to a very wide range of compound classes. Examples of compound classes to which the suitable agrochemicals may belong are: acylalanines, haloacetanilides, triazole derivatives, phosphoric acid esters, pyrethroids, benzilic acid esters, polycyclic halogenated hydrocarbons, diphenyl ether derivates, formamidines, strobilurines, aryloxyphenoxy-alkanoic acid derivatives. Examples of suitable individual compounds of the above mentioned compound classes are listed below. Where known, the common name is used to designate the individual compounds (q.v. the Pesticide Manual, 10th edition, 1994, British Crop Protection Council).

Haloacetanilides: Dimethachlor, Metolachlor, S-Metolachlor, Pretilachlor, 2-chloro-N-(1-methyl-2-methoxyethyl)-acet-2,6-xylidide, Alachlor, Butachlor, Propachlor, Dimethenamid.

Diphenyl ether derivates: Bifenox, 4-(4-Pentyn-1-yloxy) diphenylether, Acifluorfen, Oxyfluorfen, Fluoroglycofenethyl, Fomesafen, cis-trans-(±)2-ethyl-5-(4-phenoxy-phenoxymethyl)-1,3-dioxolane ("diofenolan").

Phenoxypropionic acid derivatives: Fluazifop-butyl, Haloxyfop-methyl, Haloxyfop-(2-ethoxyethyl), Fluorotopic, Fenoxapropethyl, Quizalofopethyl, Propaquizafop, Diclofop-methyl.

Acylalanines: Furalaxyl, Metalaxyl, R-Metalaxyl, Benzoylprop ethyl, Benalaxyl, Oxadixyl, Flamprop methyl.

Triazole derivatives: Difenoconazole, Etaconazol, Propiconazole, Penconazole, Triadimefon, Epoxiconazole, Tebuconazole, Bromuconazole, Fenbuconazole, Cyproconazole.

Phosphoric acid esters: Piperophos, Anilofos, Butamifos, Azamethiphos, Chlorfenvinphos, Dichlorvos, Diazinon, Methidathion, Azinpbos ethyl, Azinphos methyl, Chlorpyrifos, Chlorthiofos, Crotoxyphos, Cyanophos, Demeton, Dialifos, Dimethoate, Disulfoton, Etrimfos, Famphur, Flusulfothion, Fluthion, Fonofos, Formothion, Heptenophos, Isofenphos, Isoxathion, Malathion, Mephospholan, Mevinphos, Naled, Oxydemeton methyl, Oxydeprofos, Parathion, Phoxim, Pyrimiphos methyl, Profenofos, Propaphos, Propetamphos, Prothiophos, Quinalphos, Sulprofos, Pbemephos, Terbufos, Triazophos, Trichloronate, Fenamipos, Isazophos, s-benzyl-o,o-diisopropylphosphorothioate, Edinphos, Pyrazophos.

Pyrethroids: Allethrin, Bioallethrin, Bioresmethrin, Cyhalotrin, Cypermethrin, Deltamethrin, Fenpropathrin, Fenvalerate, s-Fenvalerate, Flucythrinate, Fluvalinate, Permethrin, Pyrethrine, Resmethrin, Tetramethrin, Tralomethrin, Ethophenprox, Cyfluthrin, Cycloprothrin, Tefluthrin, Flufenprox, Silafluofen, Bifenthrin, Fenfluthrin, Bromfenprox.

Benzilic acid esters: Brompropylate, Chlorbenzylate, Chlorpropylate.

Polycyclic halogenated hydrocarbons: Aldrin, Endosulfan.

Strobilurines: Kresoxim-methyl, Azoxystrobin (BAS 490F), Trifloxystrobin.

Miscellaneous: Tridemorph, Bromoxynil, Carboxin, Prochloraz, Propargite, Dicamba, Fenpiclonil, Fenpropimorph, Fenpropidin, Fludioxonil, Pymetrozine, Pyrifenox, Pyriproxyfen, Trinexapac-ethyl, Fluazinam, Fludioxonil, Mefenoxam, Cyprodinil, Thiabendazole, Abamectin, Emamectin benzoate, Fenoxycarb, Cyromazine, Prometryne, Ametryne, Prodiamine, Atrazine, Flumeturon, Norflurazon, Pyridate, Flumetsulam, Flumetralin, Cimectacarb, Thiamethoxam, and Acetochlor.

An especially preferred group of agrochemicals for use in the present invention include:
  Fungicides such as propiconazole, difenoconazole, fludioxonil, metalaxyl, mefenoxam (r-metalaxyl), azoxystrobin, trifloxystrobin, furalaxyl, chlorothalonil, fenpropidin, fenpropimorph, cyprodinil, oxadixyl, cyproconazole, pyrifenox, fenpiclonil, penconazole, thiabendazole, and pyroquilon;
  Insecticides such as thiamethoxam, abamectin, emamectin benzoate, cypermethrin, fenoxycarb, difenthiuron, methidathion, pymetrozine, tau-fluvalinate, lambda-cyhalothrin, permethrin, lufenuron, cyromazine, profenofos, bromopropylate, furathiocarb, organophosphorus compounds, imidacloprid, clothiadin and thiacloprid;
  Herbicides such as metolachlor, butafenacil, prometryne, chlortoluron, clodinafop, ametryne, prodiamine, flumeturon, norflurazon, pyridate, flumetsulam, acetochlor, dimethenamid, dimethachlor, fluazifop-p-butyl, pretilachlor, fenclorim;
  Growth regulators such as flumetralin and cimectacarb;
  Safeners such as fluxofenime, benoxacor, cloquintocet, dichlormid, flurazole; and
  Plant activators such as acibenzolar-s-methyl The agrochemical can be present in the present invention in a wide range of concenterations which will be dictated by the activity of the agrochemical and its relative solubility in the microemulsifiable concentrate formulation.

Suitable concentrations in relation to the composition are (% by weight of the total composition):
(a) of the hydrophobic agrochemical or mixture of hydrophobic agrochemicals: 0.1 to 25%, preferably 1 to 15%, more preferably about 1.25 to about 11.5%;
(b) of the organic solvent: 10 to 95%, preferably 20 to 65%; wherein of
  (b) (i) the alkyl alkanoate solvent: about 10 to about 35%, preferably about 15 to about 30%, more preferably about 18 to about 25% of at least one $C_{6-13}$aliphatic-$C_{1-4}$alkanoate;
  (b) (ii) the polyhydric alcohol, polyhydric alcohol condensate or mixture: about 10 to about 45%, preferably about 10 to about 40% of at least one poly$C_{2-4}$alkylene oxide, preferably an ethylene oxide, preferably having about 2 to about 20 repeating units of ethylene oxide per mole of compound;
  (b) (iii) the water-miscible solvent: about 10 to about 30%, preferably about 12 to about 25%, more preferably about 15 to about 23% of a water miscible solvent; and
(c) of the surfactants: 2 to 40%, preferably 5 to 30%; wherein of
  (c) (i) the cationic surfactant: about 0 to about 20%, preferably about 1 to about 12%, even more preferably about 2 to about 12%;
  (c) (ii) the nonionic surfactant: about 1 to about 10%, preferably about 1 to about 7%, more preferably from about 2 to about 5%, most preferably from about 2 to about 4.5%; and
  (c) (iii) the anionic surfactant: 0 to about 10%, preferably 0-9%.

Another aspect of the invention is a process for preparing a liquid microemulsifiable agrochemical concentrate as herein described, by intimateley mixing, optionally by warming, until a homogeneous phase is achieved.

In another aspect of the invention the microemulsifiable concentrate, on dilution with water, is a microemulsion useful as a ready-to-use aqueous spray mixture. Micromulsions of any required dilution can be obtained from this concentrate by dilution with water and can be used, for example, in the protection and enhancement of the health, quality and productivity and the regulation of growth of useful plants and for the control of pests such as weeds, insects, members of the order Acarina, nematodes and diseases (whether on agricultural, residential, commercial or public land). Using such dilutions it is possible to treat living plants and also plant propagation material by spraying, watering or impregnation. The microemulsions also are suitable for the protection and preservation of wood and other materials and the control of pests including but not limited to termites, ants, cockroaches, rodents, flying insects, mosquitoes, fleas and ticks in and around structures. The inventive microemulsions are also useful for nuisance fly control in farm animal premises, disease vector control, delivery of rodenticides to control rats & mice infestations, larvicides to control mosquito, and black fly infestations as well as insecticides to control crawling insects. For example, immediately before the application, the MEC of the invention may be diluted with water by simple mixing at ambient temperature in order to get a ready for use spray mixture. Generally, the agrochemical is present in the spray mixture in a concentration of from about 0.001 to about 1% by weight.

EXAMPLES

The following non-limiting examples illustrate the present invention. The invention should not be deemed limited by the examples as the full scope of the invention is defined in the claims. In the examples, all percentages are percent by weight of the total composition. The registered trademarks and other designations denote the following products.

| | | |
|---|---|---|
| 1. | Exxate 700 | Oxo-heptyl acetate |
| | Exxate 1300 | Oxo-tridecyl acetate |
| 2. | Stepan PEG 200 | Polyethylene glycol 200 |
| 3. | Witco CO360 | Polyethoxylated castor oil (36 moles EO) |
| 4. | Kessco PEG 400DL | Polyethylene glycol dilaurate ester |
| | Emerest 2620 | Polyethylene glycol monolaurate ester |
| 5. | Witco NS-500LQ | Butoxy EO/PO block copolymer EO = ethylene oxide PO = propylene oxide |
| 6. | Stepfac 8181 | Tridecyl alcohol $(EO)_6$ polyethoxylate phosphate |
| 7. | Toximul TA-2 | Polyethoxylated (2-15 moles EO) tallow fattyamine |
| | Toximul TA-5 | Polyethoxylated (5 moles of EO) tallow fattyamine |
| | Toximul TA-8 | Polyethoxylated (8 moles of EO) tallow fattyamine |
| | Toximul TA-15 | |
| 8. | Stepan Biosoft S-100 | Dodecyl benzenesulfonic acid |

Example 1

| % | Component | Type |
|---|---|---|
| 5.0 | Trifloxystrobin | Fungicide |
| 21.2 | Tetrahydrofurfuryl alcohol | Water-miscible solvent |
| 25.8 | Exxate 700 | Solvent |
| 20.0 | Stepan PEG 200 | Solvent |
| 11.9 | Witco CO360 | Nonionic surfactant |
| 2.3 | Kessco PEG 400DL | Nonionic surfactant |
| 2.2 | Witco NS-500LQ | Nonionic surfactant |
| 6.3 | Stepfac 8181 | Anionic surfactant |
| 5.3 | Toximul TA-5 | Cationic Surfactant |

Trifloxystrobin technical (52.6 grams—95.0% assay) is added to a stirred vessel containing tetrahydrofurfuryl alcohol (212 grams) and oxo-heptyl acetate (258 grams in the form of Exxate 700), and the mixture is stirred until the trifloxystrobin is dissolved. Polyethylene glycol (200 grams in the form of Stepan PEG 200), polyethoxylated castor oil (119 grams in the form of Witco $CO_{360}$), polyethylene glycol dilaurate ester (23.4 grams in the form of Kessco PEG 400DL), butoxy EO/PO block copolymer (21.9 grams in the form of Witco NS-500LQ), tridecyl alcohol polyethoxylate phosphoric acid (62.5 grams in the form of Stepfac 8181), and polyethoxylated tallow fattyamine (about 53 grams in the form of Toximul TA-5), are added and the mixture was stirred until uniform. The final pH of the mixture is controlled in the range of 4-6 by adjusting the actual amount of polyethoxylated tallow fattyamine added.

| | |
|---|---|
| Density @ 20° C. g/ml[1] | 1.017 |
| pH 1% in distilled $H_2O$[2] | 5.3 |
| Haze/ntu in 2% in $H_2O$ (50 ppm salt)[3] | 79 |

[1]Method based on ASTM D4052
[2]Method based on ASTM D1293
[3]Method based on ASTM D1889

Example 2

| % | Component | Type |
|---|---|---|
| 3.5 | Trifloxystrobin | Fungicide |
| 7.0 | Propiconazole | Fungicide |
| 20.6 | Tetrahydrofurfuryl alcohol | Water-miscible solvent |
| 18.0 | Exxate 700 | Solvent |
| 24.9 | Stepan PEG 200 | Solvent |
| 11.5 | Witco CO360 | Nonionic surfactant |
| 4.3 | Kessco PEG 400DL | Nonionic surfactant |
| 2.1 | Witco NS-500LQ | Nonionic surfactant |
| 6.1 | Stepfac 8181 | Anionic surfactant |
| 2.0 | Toximul TA-2 | Cationic Surfactant |

Propiconazole technical (72.0 grams—94.0% assay) and trifloxystrobin technical (3.6 grams—94.4% assay) are added to a stirred vessel containing tetrahydrofurfuryl alcohol (207 grams) and oxo-heptyl acetate (180 grams in the form of Exxate 700), and the mixture is stirred until the trifloxystrobin and propiconazole are dissolved. Polyethylene glycol (2489 grams in the form of Stepan PEG 200), polyethoxylated castor oil (115 grams in the form of Witco $CO_{360}$), polyethylene glycol dilaurate ester (42.7 grams in the form of Kessco PEG 400DL), butoxy EO/PO block copolymer (21.3 grams in the form of Witco NS-500LQ), tridecyl alcohol polyethoxylate phosphoric acid (60.7 grams in the form of Stepfac 8181), and polyethoxylated tallow fattyamine (about 20 grams in the form of Toximul TA-2), are added and the mixture was stirred until uniform. The final pH of the mixture should be controlled in the range of 4-6 by adjusting the actual amount of polyethoxylated tallow fattyamine added.

| | |
|---|---|
| Density @ 20° C. g/ml[1] | 1.046 |
| pH 1% in distilled $H_2O$[2] | 3.8 |
| Haze/ntu in 2% in $H_2O$ (50 ppm salt)[3] | 30 |

[1]Method based on ASTM D4052
[2]Method based on ASTM D1293
[3]Method based on ASTM D1889

Example 3

| % | Component | Type |
|---|---|---|
| 5 | Trifloxystrobin | Fungicide |
| 20.2 | Tetrahydrofurfuryl alcohol | Water-miscible solvent |
| 25.8 | Exxate 700 | Solvent |

-continued

| % | Component | Type |
|---|---|---|
| 20.0 | Stepan PEG 200 | Solvent |
| 15.8 | Witco CO360 | Nonionic surfactant |
| 2.4 | Kessco PEG 400DL | Nonionic surfactant |
| 3.8 | Witco NS-500LQ | Nonionic surfactant |
| 2.4 | Stepan Biosoft S-100 | Anionic surfactant |
| 4.6 | Toximul TA-8 | Cationic Surfactant |

Trifloxystrobin technical (52.6 grams—95.0% assay) is added to a stirred vessel containing tetrahydrofurfuryl alcohol (222 grams) and oxo-heptyl acetate (258 grams in the form of Exxate 700), and the mixture is stirred until the trifloxystrobin is dissolved. Polyethylene glycol (180 grams in the form of Stepan PEG 200), polyethoxylated castor oil (158 grams in the form of Witco $CO_{360}$), polyethylene glycol dilaurate ester (24.2 grams in the form of Kessco PEG 400DL), butoxy EO/PO block copolymer (37.8 grams in the form of Witco NS-500LQ), dodecyl benzenesulfonic acid (23.8 grams in the form of Biosoft S-100) and polyethoxylated tallow fattyamine (about 46.2 grams in the form of Toximul TA-8), were added and the mixture was stirred until uniform. The final pH of the mixture is controlled in the range of 4-6 by adjusting the actual amount of polyethoxylated tallow fattyamine added.

| | | |
|---|---|---|
| Density @ 20° C. g/ml[1] | | 1.020 |
| pH 1% in distilled $H_2O$[2] | | 4.8 |
| Haze/ntu in 2% in $H_2O$ (50 ppm salt)[3] | | 63 |

[1]Method based on ASTM D4052
[2]Method based on ASTM D1293
[3]Method based on ASTM D1889

Example 4

| % | Component | Type |
|---|---|---|
| 1.3 | Thiamethoxam | Insecticide |
| 0.2 | Abamectin | Insecticide |
| 1.0 | Butylated hydroxy toluene | Preservative |
| 15.0 | Tetrahydrofurfuryl alcohol | Water-miscible solvent |
| 18.0 | Exxate 1300 | Solvent |
| 36.5 | Stepan PEG 200 | Solvent |
| 2.0 | Emerest 2620 | Nonionic surfactant |
| 12.1 | Toximul TA-15 | Cationic surfactant |
| 6.1 | Toximul TA-5 | Cationic surfactant |
| 7.8 | Stepan Biosoft S-100 | Anionic surfactant |

Butylated hydroxy toluene (10 grams) is added to a stirred vessel containing tetrahydrofurfuryl alcohol (150 grams), oxo-tridecyl acetate (180 grams in the form of Exxate 1300) and polyethylene glycol (365 grams in the form of PEG 200). The contents are stirred until all solids are dissolved. Polyethylene glycol monolaurate ester (20.0 grams in the form of Emerest 2620), polyethoxylated tallow fattyamine (121 grams in the form of Toximul TA-15), polyethoxylated tallow fattyamine (61.0 grams in the form of Toximul TA-5), and dodecylbenzene sulfonic acid (78 grams in the form of Stepan Biosoft S100) are added and stirred until dissolution is complete. A small temperature rise is observed. Thiamethoxam technical (13.4 grams—95% assay) and abamectin technical (1.94 grams—96% assay) are added and stirred until fully dissolved. The dissolution process may require several hours.

| | | |
|---|---|---|
| Density @ 20° C. g/ml[1] | | 1.038 |
| pH 1% in distilled $H_2O$[2] | | 5.6 |

[1]Method based on ASTM D4052
[2]Method based on ASTM D1293

The eye irritancy is Caution, and it forms microemulsions that are stable for >7 days at room temperature down to 0 C in all standard testing waters, at a 5% dilution.

The preceding description of specific embodiments of the present invention is not intended to be a complete list of every possible embodiment of the invention. Persons skilled in this field will recognize that modifications can be made to the specific embodiments described here that remain within the scope of the present invention.

What is claimed is:

1. A microemulsifiable concentrate (MEC) of a hydrophobic agrochemical, said concentrate comprising in % by weight:
   (a) at least one hydrophobic agrochemical in an amount of about 0.1 to about 25% of the MEC;
   (b) a solvent system comprising:
      (i) a first solvent which is selected from the group consisting of $C_6$-$C_{13}$ alkyl $C_{1-4}$ alkanoates in an amount of about 10 to about 35% of the MEC; and
      (ii) a second solvent which is selected from the group consisting of polydric alcohols, condensates of polyhydric alcohols, and mixtures thereof in an amount of about 10 to about 45% of the MEC; and
   (c) at least one surfactant in an amount of about 1 to about 40% of the MEC, wherein the at least one surfactant includes at least one of
      (c)(i) at least one cationic surfactant selected from the group consisting of poly$C_{2-4}$alkoxylated fatty amines and
      (c)(ii) at least one nonionic surfactant selected from the group consisting of mono C2-6alkyl ether of a polyC2-4alkylene oxide block copolymer having at least a first polyalkylene oxide block region and a second polyalkylene oxide block region in which the polyalkylene oxide in said first region is different than the polyalkylene oxide in said second region, a condensation product of castor oil and a polyC2-4alkylene oxide, a mono- or di-ester of a C12-24fatty acid.

2. The MEC of claim 1 wherein said at least one surfactant (c) comprises:
   (c)(i) said at least one cationic surfactant; and
   (c)(iii) at least one anionic surfactant.

3. The MEC of claim 1 wherein said at least one surfactant (c) comprises:
   (c)(i) said at least one cationic surfactant; and
   (c)(ii) said at least one nonionic surfactant.

4. The MEC of claim 1 wherein said at least one surfactant (c) comprises:
   (c)(i) said at least one cationic surfactant;
   (c)(ii) said at least one nonionic surfactant; and
   (c)(iii) at least one anionic surfactant.

5. The MEC of claim 1 wherein said $C_6$-$C_{13}$ alkyl $C_{1-4}$ alkanoates are selected from the group consisting of $C_6$-$C_{13}$ alkyl acetates.

6. The MEC of claim 5 wherein said $C_6$-$C_{13}$ alkyl acetates are selected from the group consisting of hexyl, heptyl, octyl, 2-ethyl-hexyl, nonyl, decyl, dodecyl and tridecyl acetates.

7. The MEC of claim 1 wherein said second solvent (b)(ii) is a polyhydric alcohol.

8. The MEC of claim 1 wherein said second solvent (b)(ii) is a polyhydric alcohol condensate.

9. The MEC of claim 1 wherein said second solvent (b)(ii) is selected from the group consisting of propylene glycol; dipropylene glycol; glycerol; diethyleneglycol; polyC$_{2-6}$ alkylene glycols; mono-, di-, and tri-(polyC$_{2-6}$alkyloxylated) glycerol; sugar alcohols; mono and poly(polyC$_{2-6}$alkyloxylated) sugar alcohols; mono and poly-(hydroxyC$_{2-6}$alkyl) sugar alcohol; glyceroltriacetata; hexylene glycol (2-methyl-2,4-pentanediol); 1,3-butylene glycol; 1,2,6-hexanetriol; ethohexadiol USP (2-ethyl-1,3-hexanediol); C$_{15}$-C$_{18}$vicinal glycol; polyoxyC$_{2-6}$alkylene derivatives of trimethylolpropane; and C$_{2-6}$aliphatic glycols.

10. The MEC of claim 9 wherein said second solvent (b)(ii) is polyethylene glycol 200.

11. The MEC of claim 1 wherein said polyC$_{2-4}$alkoxylated fatty amines are selected from polyC$_{2-4}$alkoxylated C$_{14-20}$ fatty amines.

12. The MEC of claim 1 wherein said polyC$_{2-4}$alkoxylated fatty amines are selected from the group consisting of C$_{2-4}$alkoxylated tallow amine.

13. The MEC of claim 1 wherein said polyC$_{2-4}$alkoxylated fatty amines are selected from the group consisting of poly C$_{2-4}$alkoxylated fatty amines having 2-18 repeating alkoxy units per molecule.

14. The MEC of claim 13 wherein said polyC$_{2-4}$alkoxylated fatty amines are selected from the group consisting of polyC$_{2-4}$alkoxylated fatty amines having 2, 5, 8, 15, or 16 repeating alkoxy units per molecule.

15. The MEC of claim 1 wherein said at least one nonionic surfactant (c)(ii) is a mono C$_{2-6}$alkyl ether of a polyC$_{2-4}$alkylene oxide block copolymer having a C$_{2-6}$alkyl ether portion which is butyl and/or an alkylene oxide block copolymer portion which is an ethylene oxide/propylene oxide block copolymer.

16. The MEC of claim 1 wherein said at least one nonionic surfactant (c)(ii) is a mono C$_{2-6}$alkyl ether of a polyC$_{2-4}$alkylene oxide block copolymer having an alkylene oxide block copolymer portion which is an ethylene oxide/propylene oxide block copolymer in which ethylene oxide comprises from 10 mole % to 90 mole % of the block copolymer.

17. The MEC of claim 1 wherein said at least one nonionic surfactant (c)(ii) is a condensation product of castor oil and a polyC$_{2-4}$alkylene oxide having 30 to 40 alkylene oxide units per molecule.

18. The MEC of claim 1 wherein said at least one nonionic surfactant (c)(ii) is a condensation product of castor oil and a polyC$_{2-4}$alkylene oxide wherein the alkylene oxide is polyethylene oxide.

19. The MEC of claim 1 wherein said at least one nonionic surfactant (c)(ii) is a mono- or di-ester of a C$_{12-24}$fatty acid which is a mono or diester of a C$_{12-20}$fatty acid.

20. The MEC of claim 1 wherein said at least one nonionic surfactant (c)(ii) is a mono- or di-ester of a C$_{12-24}$fatty acid which is a mono or diester of a C$_{12-16}$fatty acid.

21. The MEC of claim 1 wherein said at least one nonionic surfactant (c)(ii) is a mono- or di-ester of a C$_{12-24}$fatty acid which is a mono or diester of lauric acid.

22. The MEC of claim 1 wherein said at least one nonionic surfactant (c)(ii) is a mono- or di-ester of a C$_{12-24}$fatty acid which is a polyethyleneoxide ester of a C$_{12-24}$fatty acid.

23. The MEC of claim 22 wherein said mono- or di-ester of a C$_{12-24}$fatty acid is a polyethyleneoxide ester of a C$_{12-24}$fatty acid having from about 2 to about 40 ethylene oxide units per molecule.

24. The MEC of claim 22 wherein said is a mono- or di-ester of a C$_{12-24}$fatty acid which is polyethyleneoxide mono or di lauric acid ester.

25. The MEC of claim 2 wherein said at least one anionic surfactant is selected from the group consisting of poly(oxy-1,2-ethanediyl)-alpha-C$_{10-15}$alkyl-omega-hydroxy phosphate and/or a C$_{10-13}$alkylbenzenesulfonic acid or a salt thereof.

26. The MEC of claim 25 wherein said at least one anionic surfactant is a poly(oxy-1,2-ethanediyl)-alpha-C$_{10-15}$alkyl-omega-hydroxy phosphate selected from poly(oxy-1,2-ethanediyl)-alpha-tridecyl-omega-hydroxy phosphates.

27. The MEC of claim 25 wherein said at least one anionic surfactant c(iii) is a poly(oxy-1,2-ethanediyl)-alpha-C$_{10-15}$ alkyl-omega-hydroxy phosphate having 3 to 9 repeating oxy-1,2-ethanediyl units per molecule.

28. The MEC of claim 25 wherein said at least one anionic surfactant c(iii) is a poly(oxy-1,2-ethanediyl)-alpha-C$_{10-15}$ alkyl-omega-hydroxy phosphate having 6 repeating oxy-1,2-ethanediyl units per molecule.

29. The MEC of claim 25 wherein said at least one anionic surfactant c(iii) is tridecylalcohol polyethoxylate phosphoric acid or a salt thereof.

30. The MEC of claim 25 wherein said at least one anionic surfactant c(iii) is dodecylbenzenesulfonic acid or a salt thereof.

31. The MEC of claim 1 further comprising (d) a water miscible solvent.

32. The MEC of claim 31 wherein said (d) water miscible solvent is selected from the group consisting of N—C$_{1-4}$ alkyl-2-pyrrolidones; tetramethylurea; gamma-butyrolactone; N,N-diC$_{1-4}$alkylformamides; N,N-diC$_{1-4}$alkylacetamides; dimethylsulfoxide; C$_{3-8}$cycloalkylmethanols, and monohydric C$_{1-4}$alkanols.

33. The MEC of claim 31 wherein said (d) water miscible solvent is selected from the group consisting of N-methyl-2-pyrrolidones; tetramethylurea; gamma-butyrolactone; N,N-dimethylformamides; N,N-dimethylacetamides; dimethylsulfoxide; tetrahydrofurfuryl alcohol, and ethanol.

34. The MEC of claim 31 wherein said (d) water miscible solvent is tetrahydrofurfuryl alcohol.

35. The MEC of claim 1 wherein said hydrophobic agrochemical is selected from chemical pesticides, herbicide safeners, plant growth regulators, fertilizers and nutrients, gametocides, defoliants, desiccants, and mixtures thereof.

36. The MEC of claim 35 wherein said chemical pesticides are selected from the group consisting of herbicides, algicides, fungicides, bactericides, viricides, insecticides, miticides, nematicides, molluscicides, acaricides, ectoparasiticides, and mixtures thereof.

37. The MEC of claim 1 wherein said hydrophobic agrochemical is selected from acylalanines, haloacetanilides, triazole derivatives, phosphoric acid esters, pyrethroids, benzilic acid esters, polycyclic halogenated hydrocarbons, diphenyl ether derivates, formamidines, strobilurines, phenoxypropionic acid derivatives and mxitures thereof.

38. The MEC of claim 1 wherein said hydrophobic agrochemical is selected from
(a) Haloacetanilides selected from the group consisting of Dimethachlor, Metolachlor, S-Metolachor, Pretilachlor, 2-chloro-N-(1-methyl-2-methoxyethyl)-acet-2,6-xylidide, Alachlor, Butachlor, Propachlor, Dimethenamid;
(b) Diphenyl ether derivatives selected from the group consisting of Bifenox, 4-(4-Pentyn-1-yloxy)diphenylether, Acifluorfen, Oxyfluorfen, Fluoroglycofenethyl, Fomesafen, and cis-trans-(+)-2-ethyl-5-(4-phenoxy-phenoxymethyl)-1,3-dioxolane;

(c) Phenoxypropionic acid derivatives selected from the group consisting of Fluazifop-butyl, Haloxyfop-methyl, Haloxyfop-(2-ethoxyethyl), Fluorotopic, Fenoxaprop-ethyl, Quizalofopethyl, Propaquizafop, and Diclofop-methyl;

(d) Acylalanines selected from the group consisting of Furalaxyl, Metalaxyl, R-Metalaxyl, Benzoylprop ethyl, Benalaxyl, Oxadixyl, and Flamprop methyl;

(e) Triazole derivatives selected from the group consisting of Difenoconazole, Etaconazol, Propiconazole, Penconazole, Triadimefon, Epoxiconazole, Tebuconazole, Bromuconazole, Fenbuconazole, and Cyproconazole;

(f) Phosphoric acid esters selected from the group consisting of Piperophos, Anilofos, Butamifos, Azamethiphos, Chlorfenvinphos, Dichlorvos, Diazinon, Methidathion, Azinphos ethyl, Azinphos methyl, Chlorpyrifos, Chlorthiofos, Crotoxyphos, Cyanophos, Demeton, Dialifos, Dimethoate, Disulfoton, Etrimfos, Famphur, Flusulfothion, Fluthion, Fonofos, Formothion, Heptenophos, Isofenphos, Isoxathion, Malathion, Mephospholan, Mevinphos, Naled, Oxydemeton methyl, Oxydeprofos, Parathion, Phoxim, Pyrimiphos methyl, Profenofos, Propaphos, Propetamphos, Prothiophos, Quinalphos, Sulprofos, Phemephos, Terbufos, Triazophos, Trichloronate, Fenamipos, Isazophos, s-benzyl-o,o-diisopropylphosphorothioate, Edinphos, and Pyrazophos;

(g) Pyrethroids selected from the group consisting of Allethrin, Bioallethrin, Bioresmethrin, Cyhalotrin, Cypermethrin, Deltamethrin, Fenpropathrin, Fenvalerate, s-Fenvalerate, Flucythrinate, Fluvalinate, Permethrin, Pyrethrine, Resmethrin, Tetramethrin, Tralomethrin, Ethophenprox, Cyfluthrin, Cycloprothrin, Tefluthrin, Flufenprox, Silafluofen, Bifenthrin, Fenfluthrin, and Bromfenprox;

(h) Benzilic acid esters selected from the group consisting of Brompropylate, Chlorbenzylate, and Chlorpropylate;

(i) Polycyclic halogenated hydrocarbons selected from the group consisting of Aldrin and Endosulfan;

(j) Strobilurines selected from the group consisting of Kresoxim-methyl, Azoxystrobin, Methoxyimino-{2-[1-(3-trifluoromethyl-phenyl)-ethylideneaminooxymethyl]-phenyl}-acetic acid methyl ester, and Trifloxystrobin;

(k) A miscellaneous group selected from the group consisting of Tridemorph, Bromoxynil, Carboxin, Prochloraz, Propargite, Dicamba, Fenpiclonil, Fenpropimorph, Fenpropidin, Fludioxonil, Pymetrozine, Pyrifenox, Pyriproxyfen, Trinexapac-ethyl, Fluazinam, Mefenoxam, Cyprodinil, Thiabendazole, Abamectin, Emamectin benzoate, Fenoxycarb, Cyromazine, Prometryne, Ametryne, Prodiamine, Atrazine, Flumeturon, Norflurazon, Pyridate, Flumetsulam, Flumetralin, Cimectacarb, Thiamethoxam, and Acetochlor;

(l) and mixtures thereof.

39. The MEC of claim 1 wherein said agrochemical is selected from
(a) Fungicides selected from the group consisting of propiconazole, difenoconazole, fludioxonil, metalaxyl, mefenoxam (r-metalaxyl), azoxystrobin, trifloxystrobin, furalaxyl, chlorothalonin, fenpropidin, fenpropimorph, cyprodinil, oxadixyl, cyproconazole, pyrifenox, fenpiclonil, penconazole, thiabendazole, and pyroquilon;
(b) Insecticides selected from the group consisting of thiamethoxam, abamectin, emamectin benzoate, cypermethrin, fenoxycarb, difenthiuron, methidathion, pymetrozine, tau-fluvalinate, lambda-cyhalothrin, permethrin, lufenuron, cyromazine, profenofos, bromopropylate, furathiocarb, organophosphorus compounds, imidacloprid, clothiadin and thiacloprid;
(c) Herbicides selected from the group consisting of metolachlor, S-metolachlor, butafenacil, prometryne, chlortoluron, clodinafop, ametryne, prodiamine, flumeturon, norflurazon, pyridate, flumetsulam, acetochlor, dimethenamid, dimethachlor, tralkoxydim, fluazifop-p-butyl, pretilachlor, and fenclorim;
(d) Growth regulators selected from the group consisting of flumetralin and cimectacarb;
(e) Safeners selected from the group consisting of fluxofenime, benoxacor, cloquintocet, and dichlormid;
(f) Plant activators selected from the group consisting of acibenzolar-s-methyl; and
(g) mixtures thereof.

40. The MEC of claim 1 wherein said agrochemical is selected from trifloxystrobin, propiconazole, thiamethoxam, and abamectin, and mixtures thereof.

41. The MEC of claim 1 wherein said agrochemical comprises trifloxystrobin.

42. The MEC of claim 1 further comprising a member selected from conventional agrochemical adjuncts and additives selected from antioxidants, dyes, colorants and fragrances.

43. The MEC of claim 1 wherein said at least one cationic surfactant is present in an amount of about 1% to about 20% of the MEC.

44. The MEC of claim 1 wherein said at least one nonionic surfactant is present in an amount of about 1% to about 10% of the MEC.

45. The MEC of claim 2 wherein said at least one cationic surfactant is present in an amount of about 1% to about 20% of the MEC and (c)(iii) said at least one anionic surfactant is present in an amount of 1% to 10% of the MEC.

46. The MEC of claim 3 wherein said at least one cationic surfactant is present in an amount of about 1% to about 20% of the MEC and said at least one nonionic surfactant is present in an amount of about 1% to about 10% of the MEC.

47. The MEC of claim 1 wherein said at least one surfactant (c) comprises (c)(i) said at least one cationic surfactant in an amount of about 1% to about 20% of the MEC; (c)(ii) said at least one nonionic surfactant in an amount of about 1% to about 10% of the MEC; and (c)(iii) at least one anionic surfactant which is present in an amount of up to about 10% of the MEC.

48. The MEC of claim 1 having a pH of about 3 to about 7.

49. The MEC of claim 1 having a pH of 4 to 6.

50. The MEC of claim 1 which has a density of about 0.9 to about 1.1 g/ml.

51. The MEC of claim 50 that has a droplet particle size of about 20 to 300 nm.

52. A microemulsion comprising an MEC of claim 1 and water.

53. The microemulsion of claim 52 in the form of a sprayable composition.

54. The microemulsion of claim 53 which is in a ready to use sprayable form.

55. A method of dispensing a hydrophobic agrochemical comprising preparing a MEC of claim 1, contacting said MEC with water to result in an aqueous microemulsion thereof, and dispensing said aqueous microemulsion.

56. The method of claim 55 wherein said MEC is contacted with a first fraction of said water to prepare a microemulsion concentrate thereof and said microemulsion concentrate is further diluted with an additional fraction of water to result in said final microemulsion whereby said final microemulsion may result before or during the act of dispensing said agrochemical.

57. A method of treating a plant with an agrochemical comprising preparing a MEC of claim 1, diluting said MEC with an amount of water to form a microemulsion, and exposing said plant or portion of said plant to said microemulsion.

58. A method of treating soil with an agrochemical in preparation for planting comprising preparing a MEC of claim 1, diluting said MEC with an amount of water to form a microemulsion, and exposing said soil to said microemulsion.

59. A method of treating a seed with an agrochemical comprising preparing a MEC of claim 1, diluting said MEC with an amount of water to form a microemulsion, and exposing said seed to said microemulsion.

60. A method of pre-emergent treatment of planted crops with an agrochemical comprising preparing a MEC of claim 1, diluting said MEC with an amount of water to form a microemulsion, and exposing said pre-emergent crop area to said microemulsion.

61. A plant or plant part treated with a microemulsion of an agrochemical, said microemulsion being an aqueous dilution of an MEC of claim 1.

* * * * *